United States Patent
Shmulewitz

[19]

[11] Patent Number: 5,961,548
[45] Date of Patent: Oct. 5, 1999

[54] BIFURCATED TWO-PART GRAFT AND METHODS OF IMPLANTATION

[76] Inventor: Ascher Shmulewitz, 4338 W. Mercer Way, Mercer Island, Wash. 98040

[21] Appl. No.: 08/972,371

[22] Filed: Nov. 18, 1997

[51] Int. Cl.[6] ...................................................... A61F 2/06
[52] U.S. Cl. ................................ 623/1; 623/12; 606/191; 606/198
[58] Field of Search ............................. 623/1, 12; 621/1; 606/191, 198

[56] References Cited

U.S. PATENT DOCUMENTS

| | | | |
|---|---|---|---|
| 4,503,569 | 3/1985 | Dotter | 3/1.4 |
| 4,553,545 | 11/1985 | Maass et al. | 128/341 |
| 4,562,596 | 1/1986 | Kornberg | 623/1 |
| 4,577,631 | 3/1986 | Kreamer | 623/1 |
| 4,820,298 | 4/1989 | Leveen et al. | 623/1 |
| 5,246,445 | 9/1993 | Yachia et al. | 606/108 |
| 5,387,235 | 2/1995 | Chuter | 623/1 |
| 5,443,500 | 8/1995 | Sigwart | 623/1 |
| 5,575,817 | 11/1996 | Martin | 623/1 |
| 5,609,627 | 3/1997 | Goicoechea et al. | 623/1 |
| 5,653,743 | 8/1997 | Martin | 623/1 |
| 5,709,713 | 1/1998 | Evans et al. | 623/1 |
| 5,755,772 | 5/1998 | Evans et al. | 623/1 |
| 5,833,669 | 11/1998 | Chuter | 623/1 |
| 5,843,160 | 12/1998 | Rhodes | 623/1 |

*Primary Examiner*—David H. Willse
*Assistant Examiner*—Sozette J. Jackson
*Attorney, Agent, or Firm*—Fish & Neave; Nicole A. Pisano

[57] ABSTRACT

A bifurcated graft comprising two sections is provided that is implanted in two consecutive steps in a bifurcated body lumen. A first section of the graft comprises a main portion having a joining region and a first leg extending from the main portion adjacent to the joining region. The main portion of the graft is implanted in the body lumen upstream of the bifurcation, while the first leg extends into a first branch of the body lumen. A second section of the graft, which is implanted in a separate step, comprises second a leg that extends into the second branch of the body lumen and a proximal portion that interconnects with the joining region of the first section.

17 Claims, 4 Drawing Sheets

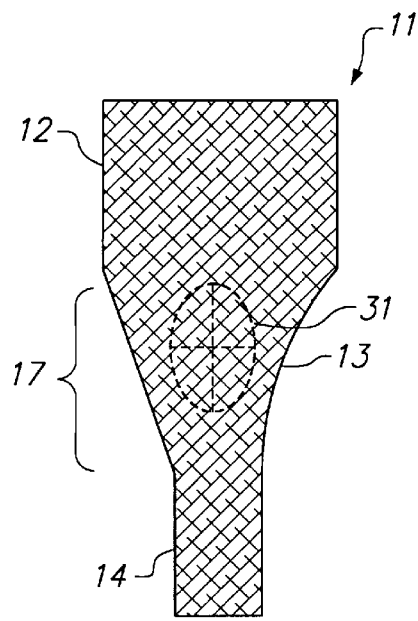
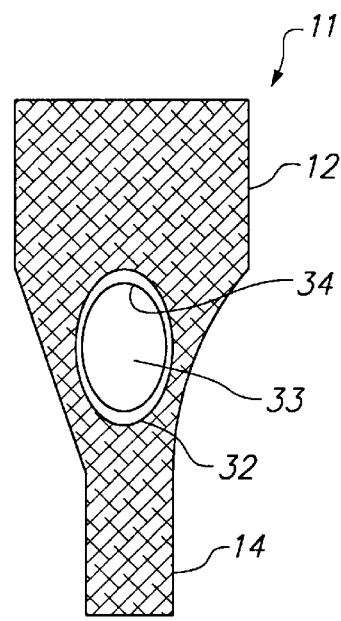
FIG. 3A    FIG. 3B
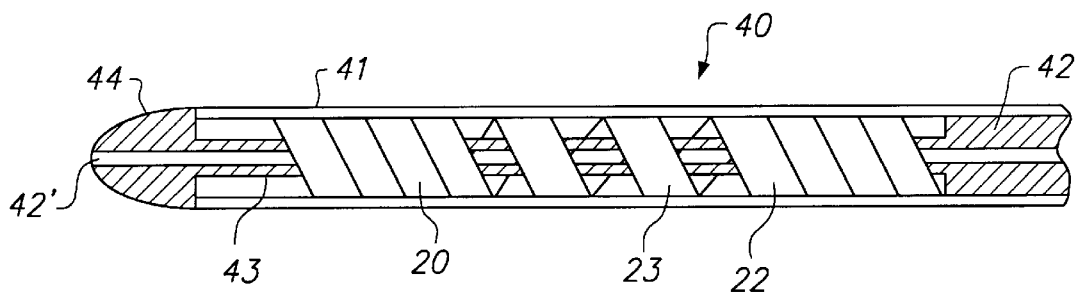
FIG. 4
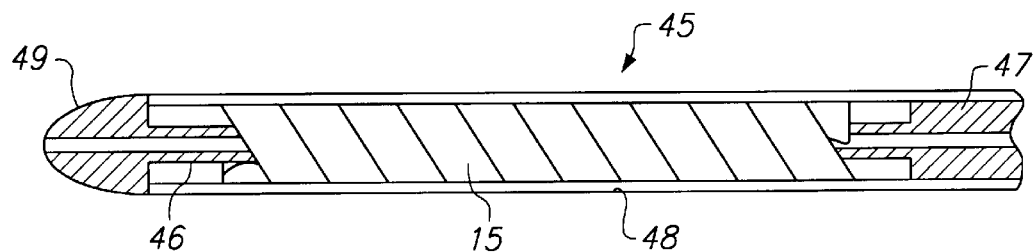
FIG. 5

5,961,548

BIFURCATED TWO-PART GRAFT AND METHODS OF IMPLANTATION

FIELD OF THE INVENTION

The present invention relates generally to intraluminal grafts for maintaining the patency of bifurcated body lumens. More specifically, the present invention is directed to bifurcated graft that includes a first section extending from a main lumen into a first branch lumen, and a second separately implanted section that connects to the first section and extends into a second branch lumen.

BACKGROUND OF THE INVENTION

A number of prostheses are known from treating the formation of aneurysms in bifurcated body lumens. A typical previously known bifurcated prosthesis comprises a hollow tubular graft having a main section and first and second legs. During open surgery, for example, to repair an abdominal aortic aneurysm, the main section is sutured to the aorta below the renal arteries, and the first and second branches of the graft are sutured to the corresponding iliac arteries. Because surgical implantation of previously known prostheses poses a major risk of mortality, such surgery frequently cannot be performed on patients in poor health.

In attempting to overcome the drawbacks associated with surgically implanted grafts, a number of methods and apparatus have been developed to implant such grafts percutaneously. Kornberg U.S. Pat. No. 4,562,596, describes a bifurcated graft for intraluminal, percutaneous implantation. The graft comprises a hollow tubular main portion connected to a first leg and a shorter second leg. The main portion includes a plurality of barbs that impale the healthy tissue of the aorta to retain the graft in position. A drawback of such grafts, however, is the inability to provide a fluid tight seal at the ends of the graft. Without adequate sealing, bypass flow paths may develop between the graft and the tissue which may eventually cause rupture of the aneurysm.

Chuter U.S. Pat. No. 5,387,235 describes a bifurcated graft having a main portion connected to first and second legs. Each of the main portion and first and second legs includes a barbed self-expanding anchor ring that engages healthy tissue in either the aorta or the iliac arteries to retain the graft in position. A drawback of devices of this type, however, is that the diameter of the delivery system must be large enough to accommodate the combined diameters of each of the anchor deployment mechanisms. Thus, for example, it may not be possible to use the device described in the Chuter patent in patients having small diameter femoral arteries.

Yet another drawback of previously known bifurcated grafts is the difficulty encountered in pulling the legs of the graft into the branch vessels. While a number of prior art methods have been developed for accomplishing this task, these generally involve snaring a guide wire, either in the iliac artery or in the abdominal aorta, to place a guide wire for deploying the leg of the graft in the contralateral branch.

In view of the foregoing, it would be desirable to provide a bifurcated graft, and methods of implantation, that provide positive sealing between the graft and healthy tissue proximal and distal of the graft site.

It also would be desirable to provide a bifurcated graft, and methods of implantation, that enable smaller diameter delivery systems to be employed than heretofore possible.

It further would be desirable to provide a bifurcated graft, and methods of implantation, that enhance the ease with which the legs of the graft may be deployed in the branches of a bifurcated body lumen.

SUMMARY OF THE INVENTION

In view of the foregoing, it is an object of the present invention to provide a bifurcated graft, and methods of implantation, that provide positive sealing between the graft and healthy tissue proximal and distal of the graft site.

It is another object to the invention to provide a bifurcated graft, and methods of implantation, that enable smaller diameter delivery systems to be employed than in previously known bifurcated graft systems.

It is yet another object of the invention to provide a bifurcated graft, and methods of implantation, that enhance the ease with which the legs of the graft may be deployed in the branches of a bifurcated body lumen.

These and other objects of the invention are accomplished by providing a bifurcated graft comprising two sections that are implanted in two consecutive steps in a bifurcated body lumen. A first section of the graft comprises a main portion having a joining region and a first leg extending from the main portion adjacent to the joining region. The main portion of the graft is implanted in the trunk of the body lumen, upstream of the bifurcation, while the first leg extends into a first branch of the body lumen. A second section of the graft, implanted in a separate step, comprises a second leg that extends into the second branch of the body lumen and a proximal portion that interconnects with the joining region of the first section.

In one embodiment, helical coils are employed in the first and section sections of the graft to support and anchor the first and second sections into the body lumen. The helical coils, which may be formed of biocompatible material, such as a stainless steel or nickel-titanium alloy, is preferably covered by biocompatible graft material, such as polyester material or polytetrafluoroethylene (PTFE). The helical coils may be either self-expanding or thermally activated.

In accordance with the methods of the present invention, the graft of the present invention is advantageously inserted transluminally and percutaneously in separate sections, which are then joined together within the bifurcation of the body lumen. Because the first section and second section are separately implanted, for example, through the ranches of the body lumen, the delivery systems employed for the first and second graft sections may have substantially smaller diameters than previously known graft systems.

BRIEF DESCRIPTION OF THE DRAWINGS

Further features of the invention, its nature and various advantages will be more apparent from the accompanying drawings and the following detailed description of the preferred embodiments, in which:

FIGS. 2A–2C are, respectively, a side and end view of the helical coil support of the first section of the graft of FIG. 1, while FIG. 2C is a side view of the helical coil support of the second section of the graft of FIG. 1;

FIGS. 3A and 3B are views of alternative embodiments, taken along view lines 3—3 of FIG. 1, of the first section of the graft showing alternative joining regions constructed in accordance with the present invention.

FIG. 4 is a side view, partly in section, of the first section of the graft of FIG. 1 disposed within a delivery catheter in its contracted state;

FIG. 5 is a side view, partly in section, of the second section of the graft of FIG. 1 disposed within a delivery catheter in its contracted state.

DETAILED DESCRIPTION OF THE INVENTION

The present invention provides a graft for treating bifurcated body lumens, such as the bifurcation between the abdominal aorta and the iliac arteries, or between the common carotid artery and its internal and external branches. In accordance with the methods of the present invention, the graft is percutaneously implanted in two separate sections, thereby enabling the delivery catheters employed for the respective sections to be substantially smaller than used in previously known bifurcated graft systems.

Figure 1:
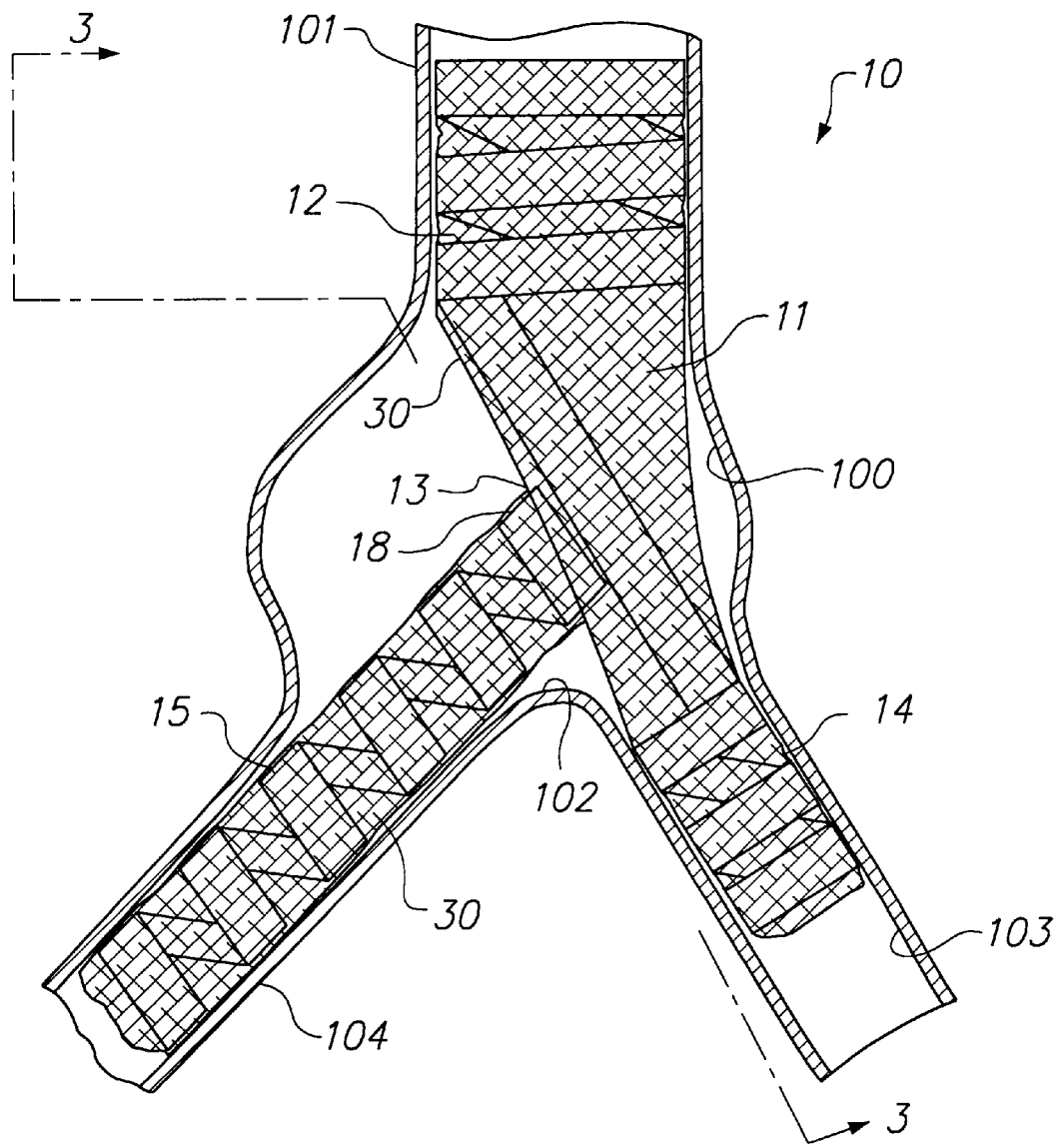
FIG. 1 is a side view of an illustrative embodiment of a two-part graft constructed in accordance present invention shown in its assembled state.

Referring to FIG. 1, graft 10 constructed in accordance with the present invention is described. Graft 10 includes first section 11 having main portion 12 and joining region 13 that are disposed in trunk 101 of body lumen 100 upstream of bifurcation 102. First leg 14 extends from main portion 12 adjacent to joining region 13 and into first branch 103 of body lumen 100. Second section 15 interconnects with main portion 12 at joining region 13, and extends into second branch 104 of body lumen 100. In accordance with the methods of the present invention, first section 11 is implanted in the body region so as to extend from trunk 101 to first branch 103. Second section 15 is then implanted using a separate delivery catheter so that second section 15 is disposed through joining region 13 and extending into second branch 104. Second section 15 provides a fluid tight seal with the main portion 12 where it connects to joining region 13.

Figure 2A:
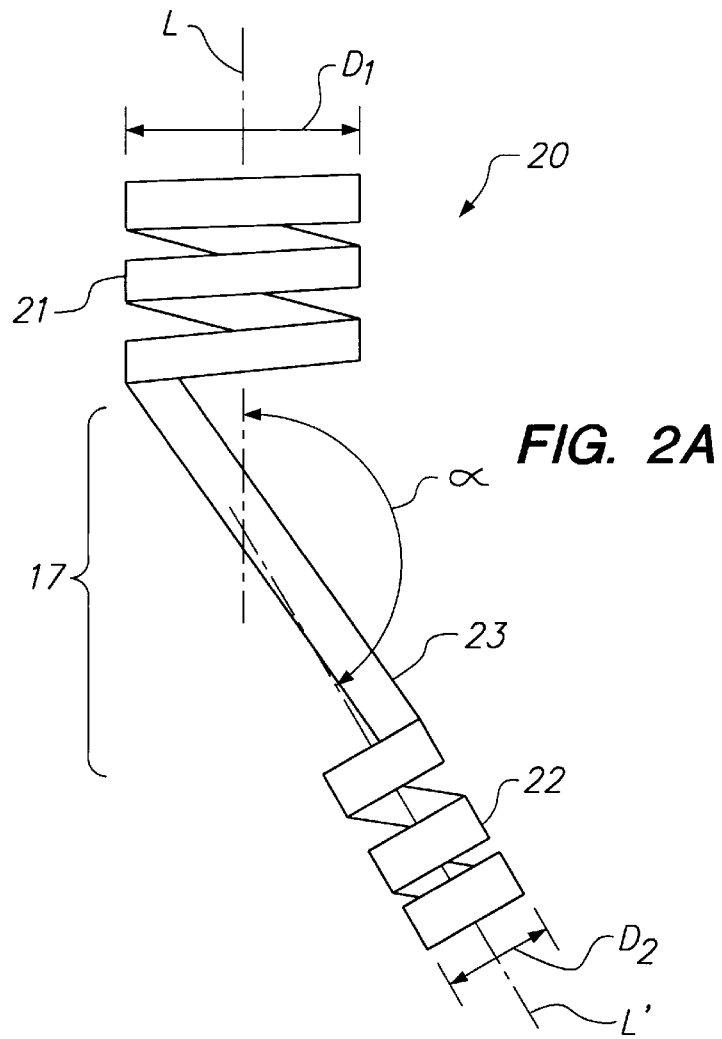
Figure 2B:
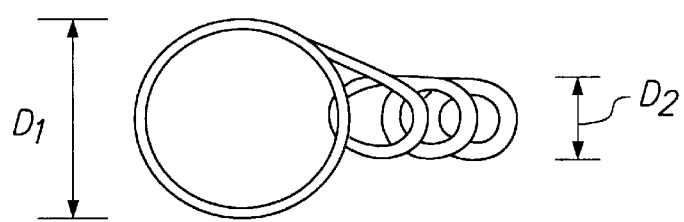

Referring to FIGS. 1, 2A and 2B, the first section of graft 10 comprises helical coil 20 having laterally and longitudinally offset coil portions 21 and 22 covered with biocompatible graft material 30 (graft material 30 omitted from FIGS. 2A and 2B for clarity). Coil portion 21 preferably has diameter $D_1$ large enough so that, when first section 11 is deployed, coil portion 21 engages trunk 101 of body lumen 100 to provide a fluid tight seal between graft material 30 and body lumen 100. Coil portion 22 has diameter $D_2$ smaller than diameter $D_1$ of coil portion 21, and is dimensioned to sealing engage graft material 30 to the walls of branch 103 of the body lumen.

Biocompatible graft material 30, preferably PTFE or a previously known graft material (e.g., a polyester fiber) provides a fluid tight passageway when graft 10 is deployed and fully assembled in body lumen 100. Coil portions 21 and 22 are offset from one another both laterally and longitudinally by strut 23 to form gap 17. As illustrated in FIG. 2A, the longitudinal axes L and L' of coil portions 21 and 22, respectively, may be inclined at an angle α to one another. Gap 17 coincides with joining region 13 and enables second section 15 to be interconnected with the first section.

Figure 2C:
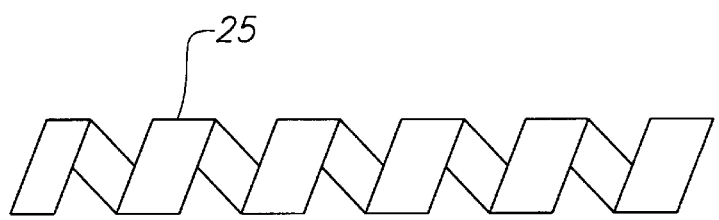

Second section 15, shown in FIGS. 1 and 2C, likewise comprises helical coil 25 covered with biocompatible graft material 30, and may have an expanded diameter sufficient to engage graft material 30 to the walls of the branch 104 of the body lumen (graft material 30 omitted from FIG. 2C for clarity). Outside of gap 17, helical coil 20, and helical coil 25, may have either a constant or variable pitch (i.e., spacing between adjacent turns of the coil).

Helical coils 20 and 25 preferably comprise stainless steel or nickel-titanium alloys. Helical coils 20 and 25 may be either self-expanding or exhibit mechanical or thermally activated shape memory behavior. Examples of such coils are described, for example, in Maass U.S. Pat. No. 4,553, 545, Yachia et al. U.S. Pat. No. 5,246,445 and Dotter U.S. Pat. No. 4,503,569, which are incorporated herein by reference. All of these helical coil designs permit the coils to be wound down (or compressed) to a small diameter for insertion in a small diameter delivery catheter. Alternatively, helical coils 20 and 25, such as described in Sigwart U.S. Pat. No. 5,443,500, could be employed. Biocompatible graft material 30 is attached to the interior or exterior surface of helical coils 20 and 25, for example, using a biocompatible adhesive, sutures or other suitable means.

Referring now to FIGS. 3A and 3B, embodiments of graft 10 having alternative joining regions 13 are described. In both of the embodiments of FIGS. 3A and 3B, joining region 13 comprises a portion of graft material 30 of first section 11 adapted to interconnect with the second section 15 of graft 10. In FIG. 3A, joining region 13 comprises weakened or perforated portion 31 of graft material 30 in the region of gap 17, so that proximal end 18 of second section 15 may be inserted into fluid communication with main portion 12.

Alternatively, as shown in FIG. 3B, joining region 13 may include retention collar 32 surrounding opening 33 to provide a fluid tight seal at the point of interconnection between second section 15 and main portion 12. Retention collar 32 provides solid perimeter 34 against which proximal end 18 of second section 15 may expand, and reduces the potential for the proximal end of second section 15 to tear graft material 30 in joining region 13 during deployment. If provided, retention collar 32 may comprise a double thickness or pleated portion of the graft material, or an elastomeric or biocompatible plastic band.

In FIGS. 4 and 5, first section 11 and second section 15 of graft 10 are shown loaded within delivery catheters 40 and 45 (graft material 30 omitted for clarity). Delivery catheter 40 comprises outer sheath 41 enclosing deployment member 42 having guide wire lumen 42', reduced diameter portion 43 and nose cone 44, and may be similar in construction to that described, for example, in Garza et al. U.S. Pat. No. 4,665, 918, the entirety of which is incorporated herein by reference. First section 11 of graft 10 is disposed about reduced diameter portion 43 of deployment member 42, and then compressed (or wound) down onto portion 43 so that the deployment member may be withdrawn within outer sheath 41. As illustrated in FIG. 4, in the constrained state, gaps may develop between turns of strut 23, while turns of coil portions 21 and 22 may overlap.

During the process of compressing or winding the first section onto reduced diameter portion 43 of deployment member 42, graft material 30 is twisted, stretched, or compressed as needed to conform to the reduced diameter of the helical coil. Likewise, second section 15 is compressed or wound to its delivery diameter (including manipulation of the graft material 30) on reduced diameter portion 46 of deployment member 47, and then constrained in that position by being withdrawn within outer sheath 48.

Figure 6A:
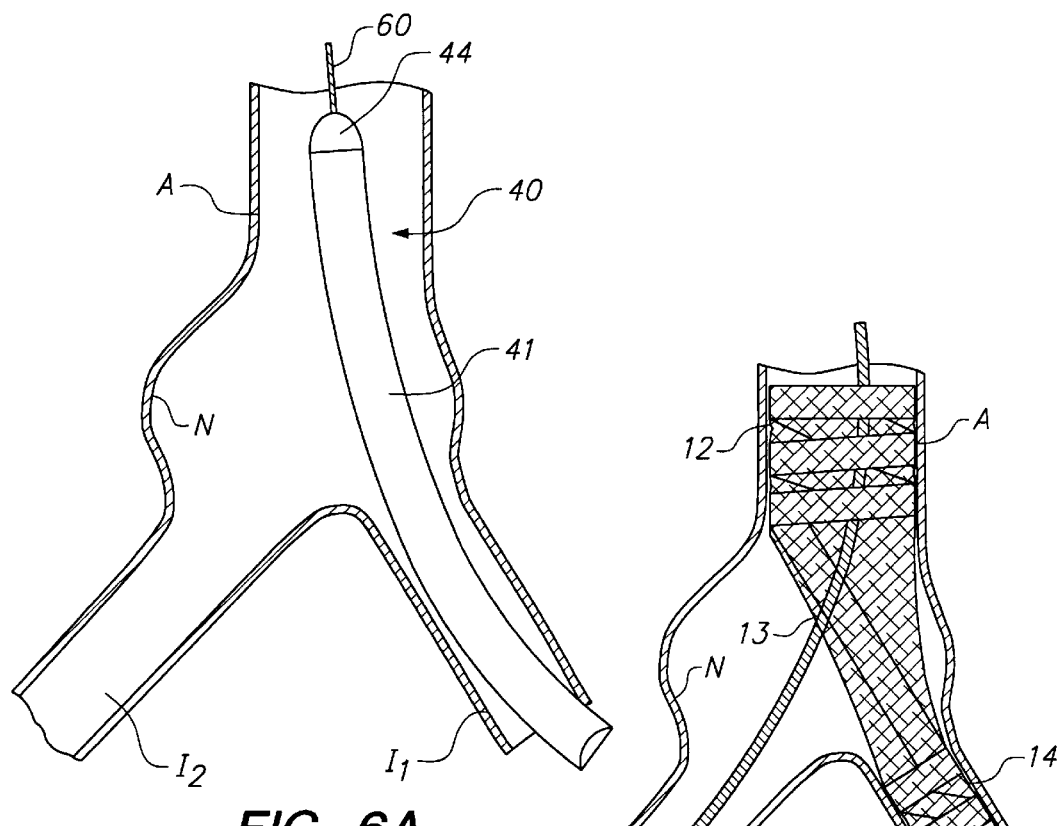
FIGS. 6A–6C are views of the steps of implanting the graft of FIG. 1.
Figure 6B:
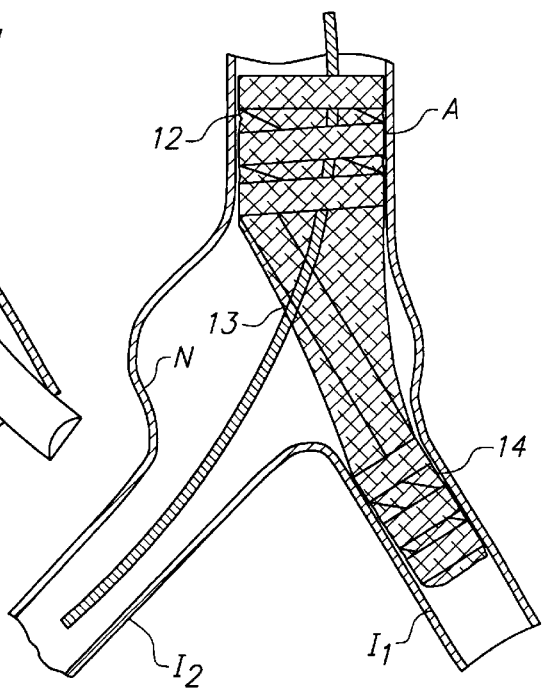
Figure 6C:
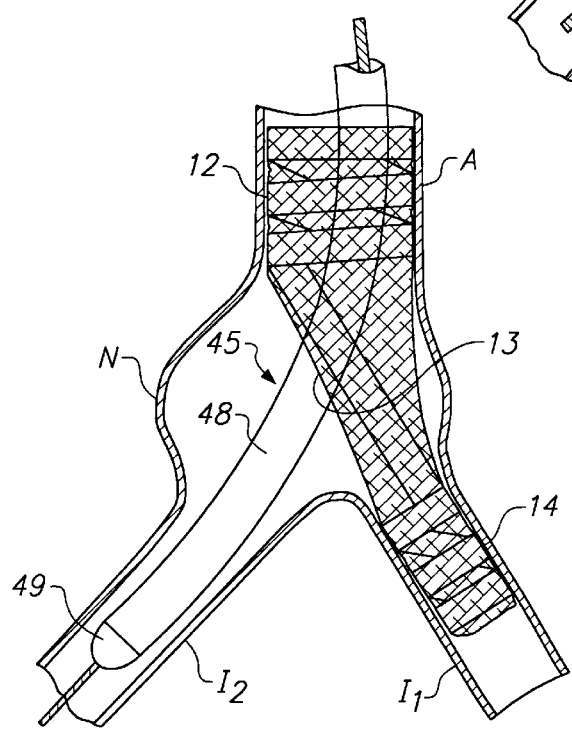

Referring now to FIGS. 6A to 6C, illustrative methods of implanting graft 10 in a bifurcated body lumen in accordance with the present invention are described. In particular, FIGS. 6A to 6C show exemplary steps for implanting graft 10 of the present invention in abdominal aorta A and iliac arteries $I_1$, $I_2$ to treat an abdominal aortic aneurysm N. Other methods of employing graft 10, for example, in the carotid arteries, will become apparent based on the following description.

In FIG. 6A, delivery catheter 40, containing first section 11 in a contracted state, is first inserted transluminally and percutaneously along guide wire 60 into abdominal aorta A via a femoral artery or a surgical cut-down. Delivery catheter 40 may include suitable markers that are visible under a fluoroscope, so that placement of the delivery catheter may be visually confirmed. Outer sheath 41 is then retracted while deployment member 42 is retained in position.

As first section 11 of graft 10 expands, main portion 12 engages the trunk of the aorta A, while first leg 14 engages the wall of first iliac artery $I_1$ distal to the aneurysm. Delivery catheter 40 and guide wire 60 are then withdrawn. First section 11 may fully expand, mechanically or by thermal activation, to its deployed condition. Alternatively, helical coil 20 of first section 11 may partially self-expand and then be fully deployed using a dilatation device, such as a balloon catheter inserted along guide wire 60 (in the latter case guide wire 60 is not withdrawn with delivery catheter 40).

In FIG. 6B, guide wire 65 is advanced via the subclavian artery, or a surgical cut-down, through main portion 12 of first section 11 until it engages and perforates (or passes through) joining region 13. Guide wire 65 is then advanced so that it extends into the contralateral iliac artery.

In FIG. 6C, delivery catheter 45 is shown inserted along guide wire 65, so that nose cone 49 pierces perforation 31 in graft material 30 (or passes through opening 33 in retention collar 32) in joining region 13 provided for that purpose (see FIGS. 3A and 3B). Delivery catheter 45 is then positioned so that the distal end of second section 15 is disposed within second iliac artery $I_2$ distal to aneurysm N, and the proximal end is disposed within joining region 13. Once placement of second section 15 is confirmed, for example, by fluoroscopic techniques, or angiography, outer sheath 48 is withdrawn while deployment member 47 is retained in position.

When outer sheath 48 is retracted, helical coil 25 of second section 15 expands from its contracted state to its deployed state. In its deployed state, the distal end of second section 15 engages second iliac artery $I_2$ distal to aneurysm N, while the proximal end engages graft material 30 in joining region 13 of first section 11, thus forming an inverted Y shape, as shown in FIG. 1. Helical coil 25 may either fully expand, mechanically or by thermal activation, or may partially expand upon being released from outer sheath 48. As for the helical coil of first section 11, in this latter case the graft section may be fully expanded into position using a dilatation device, such as a balloon catheter.

Upon completion of the second step of the implantation procedure, delivery catheter 45 and guide wire 65 are withdrawn from the patient. As described hereinabove, graft 10 may be used to reline a bifurcated body lumen to provide a new passageway for blood flow that relieves pressure from an aneurysm, thereby reducing the risk of rupture.

As will be apparent to one of skill in the art, graft 10 may be deployed in methods other than that described hereinabove. For example, rather than inserting delivery catheter 45 through main portion 12 of the first section, the clinician might instead capture and pull the end of guide wire 65 out of the patient's body via an opening in the contralateral femoral artery. Thereafter, delivery catheter 45 may be inserted retrograde transluminally along guide wire 65 to position and deploy second section 15 between joining region 13 and the second iliac artery. In this manner, the second section may be delivered from beneath the joining section by passing through the second branch of the bifurcation, rather than by passing through main portion 12 as in FIG. 6C.

While preferred illustrative embodiments of the present invention are described above, it will be apparent to one skilled in the art that various changes and modifications may be made therein without departing from the invention, and it is intended in the appended claims to cover all such changes and modifications which fall within the true spirit and scope of the invention.

What is claimed is:

1. Apparatus for reinforcing a bifurcated lumen having a trunk and a bifurcation forming first and second branches, the apparatus comprising:

a first section, configured to be positioned within the trunk and first branch of the bifurcated lumen, comprising:

a main portion configured to fit within the trunk upstream of the bifurcation;

a first leg configured to extend into the first branch when the first section is positioned in the trunk, and a joining region disposed adjacent to the first leg, the joining region configured to align with the second branch when the first section is positioned in the trunk.

2. The apparatus as defined in claim 1, further comprising a second section configured to be positioned separately within the second branch and interconnected to the joining region of the first section, the second section extending into the second branch.

3. The apparatus as defined in claim 2, wherein the first section and the second section form an inverted Y-shape when joined.

4. The apparatus as defined in claim 3, wherein the first and second sections each comprise graft material attached to a support.

5. The apparatus as defined in claim 4, wherein the support comprises a compressible and expandable helical coil.

6. The apparatus as defined in claim 5, wherein the helical coil comprises a shape-memory material.

7. The apparatus as defined in claim 4, wherein the graft material is selected from the group consisting of polyester fiber and PTFE.

8. The apparatus as defined in claim 4 wherein the support comprises a self-expanding helical coil.

9. The apparatus as defined in claim 1 wherein the first section comprises a first helical coil connected to a second helical coil.

10. The apparatus as defined in claim 9, wherein the first coil has a first longitudinal axis and the second coil has a second longitudinal axis, the first longitudinal axis spaced apart from the second longitudinal axis.

11. The apparatus as defined in claim 10 wherein the first longitudinal axis is inclined at an angle to the second longitudinal axis.

12. The apparatus as defined in claim 1 wherein the joining region comprises a weakened or perforated region of the graft material.

13. The apparatus as defined in claim 1 wherein the joining section further comprises a retention collar.

14. The apparatus as defined in claim 13 wherein the retention collar comprises an elastomeric band.

15. Apparatus for reinforcing a bifurcated lumen having a trunk and a bifurcation forming first and second branches, the apparatus comprising:

a first section having a main portion configured to fit within the trunk upstream of the bifurcation, a first leg configured to extend into the first branch when the first section is positioned in the trunk, and a joining region disposed adjacent to the first leg; and a second section configured to be positioned separately within the second branch and interconnected to the joining region of the first section, the second section extending into the second branch.

16. The apparatus as defined in claim 15, wherein the first and second sections each comprise graft material attached to a helical coil support.

17. The apparatus as defined in claim 16, wherein the helical coil supports comprise a shape-memory material and the graft material is selected from the group consisting of polyester fiber and PTFE.

* * * * *